(12) United States Patent
Ohara

(10) Patent No.: US 7,820,733 B2
(45) Date of Patent: Oct. 26, 2010

(54) DENTAL POLYMERIZABLE CORE BUILD-UP MATERIAL OF SEPARATELY PACKED TYPE

(75) Inventor: Yasujiro Ohara, Chiyoda-ku (JP)

(73) Assignee: Kuraray Medical Inc., Kurashiki-shi (JP)

( * ) Notice: Subject to any disclaimer, the term of this patent is extended or adjusted under 35 U.S.C. 154(b) by 471 days.

(21) Appl. No.: 11/575,356

(22) PCT Filed: Sep. 1, 2005

(86) PCT No.: PCT/JP2005/015986

§ 371 (c)(1),
(2), (4) Date: Mar. 15, 2007

(87) PCT Pub. No.: WO2006/030645

PCT Pub. Date: Mar. 23, 2006

(65) Prior Publication Data

US 2007/0249752 A1 Oct. 25, 2007

(30) Foreign Application Priority Data

Sep. 16, 2004 (JP) ............................. 2004-270202

(51) Int. Cl.
*A61K 6/083* (2006.01)
*A61C 5/04* (2006.01)
(52) U.S. Cl. .................... 523/116; 433/228.1; 523/118
(58) Field of Classification Search ................. 523/116; 433/228.1
See application file for complete search history.

(56) References Cited

U.S. PATENT DOCUMENTS

| | | | | |
|---|---|---|---|---|
| 5,228,907 A | * | 7/1993 | Eppinger et al. | 106/35 |
| 5,861,445 A | * | 1/1999 | Xu et al. | 523/116 |
| 6,121,344 A | | 9/2000 | Angeletakis et al. | |
| 6,221,931 B1 | * | 4/2001 | Sakuma et al. | 523/116 |
| 6,326,417 B1 | * | 12/2001 | Jia | 523/116 |
| 6,797,767 B2 | * | 9/2004 | Stannard et al. | 524/559 |
| 2005/0250868 A1 | * | 11/2005 | Suzuki et al. | 522/25 |

FOREIGN PATENT DOCUMENTS

| | | |
|---|---|---|
| DE | 699 21 943 | 12/2005 |
| EP | 1 050 291 A2 | 11/2000 |
| JP | 2-250808 | 10/1990 |
| JP | 8-308861 | 11/1996 |
| JP | 11-335220 | 12/1999 |
| JP | 2000-327514 | 11/2000 |
| JP | 2001-302429 | 10/2001 |
| JP | 2002-518309 | 6/2002 |
| JP | 2005-170813 | 6/2005 |
| WO | WO 99/65453 | 12/1999 |

* cited by examiner

*Primary Examiner*—Tae H Yoon
(74) *Attorney, Agent, or Firm*—Oblon, Spivak, McClelland, Maier & Neustadt, L.L.P.

(57) ABSTRACT

The invention provides a divided type dental polymeric core build-up material including a first paste (A) and a second paste (B), in which each of the pastes is a paste obtained by mixing at least a (meth)acrylate monomer, a filler having a particle size distribution within a range of 0.1 through 40 μm and an average particle diameter of 0.7 through 10 μm, and a fine particle filler having an average particle diameter of primary particles of 0.001 through 0.050 μm, and having a viscosity at 25° C. of 280 through 470 P, and in which one of the pastes includes an oxidant and the other includes a reductant and at least one of the pastes includes a photopolymerization catalyst. The divided type dental polymeric core build-up material of this invention has high operability in core build-up and forms a polymerically cured substance with a good mechanical property.

15 Claims, No Drawings

US 7,820,733 B2

DENTAL POLYMERIZABLE CORE BUILD-UP MATERIAL OF SEPARATELY PACKED TYPE

TECHNICAL FIELD

The present invention relates to a divided type dental polymeric core build-up material, and more particularly it relates to a divided type dental polymeric core build-up material composed of two pastes that is highly operable in core build-up and is capable of forming an abutment with a good mechanical property after polymerization.

BACKGROUND ART

Recently, a polymeric composition including a polymeric monomer, a filler a polymerization initiator and so on is widely used as a repairing material in clinical dentistry. When dental polymeric compositions are classified depending upon the type of polymerization initiator, namely, the type of polymerization method, they are classified into photopolymerization type compositions, chemical polymerization type compositions and dual cure type compositions cured through both photopolymerization and chemical polymerization. Alternatively, when the dental polymeric compositions are classified depending upon the packing form, they are classified into one-paste type compositions and two-paste type compositions.

A photopolymerization type composition using a photopolymerization catalyst as a polymerization initiator is a 1-paste type composition. Owing to recently remarkably developed light irradiators, a photopolymerization type composition is widely used in the clinical dentistry. However, a photopolymerization type composition cannot be used for a repair portion that cannot be irradiated with light of a light irradiator, such as a bottom of a root canal portion or an inner face of the repairing material.

With respect to a chemical polymerization type composition or a dual cure type composition using, as a polymerization initiator, a redox catalyst composed of an oxidant and a reductant, the oxidant and the reductant are preferably packed in different packages for securing storage stability. Therefore, such a composition is generally a two-divided type composition, namely, a two-paste type composition.

In using a chemical polymerization type composition, two kinds of pastes are mixed with a tool such as a spatula or a mixing rod so as to cause a reaction between the oxidant and the reductant, and thus, the composition is polymerically cured. Although a chemical polymerization type composition can be advantageously used in a repair portion that cannot be irradiated with light, it is disadvantageously difficult to adjust its polymeric curing time.

A dual cure type composition is a dental polymeric composition developed for overcoming the disadvantage of the chemical polymerization type composition. In a dual cure type composition, a portion that cannot be irradiated with light is cured by using a redox catalyst, and a portion that can be irradiated with light is cured in a short period of time by using a photopolymerization catalyst that can be easily adjusted in the polymeric curing time. A dual cure type composition is also used as a core build-up material for repairing a root canal portion in which a root canal is formed after taking out a dental pulp of a tooth root where dental caries has been seriously advanced.

Examples of a commercially available dual cure type core build-up composition of the two-paste type are "UniFil-Core" (manufactured by GC Corporation; trade name), "LuxaCore-Dual" (manufactured by Dental-Material Gesselschaft mbH; trade name) and "Build-it FR" (manufactured by Generic Pentron; trade name).

On the other hand, Patent Document 1 describes a dental curable composition including a polymeric monomer, a filler with an average particle diameter of 0.05 through 1 μm, a fine particle filler with an average particle diameter smaller than 0.05 μm and a polymerization initiator. The curable composition described in Patent Document 1 is applied on a tooth neck or a tooth root in a small thickness with a small brush or the like, so as to form a cured coat on the tooth neck or the tooth root. Therefore, it is significant that the composition has both such low viscosity that it can be applied in a small thickness with a small brush and such low flowability that it can be prevented from flowing when applied. It is noted that Patent Document 1 does not mention a core build-up material at all and describes neither that the curable composition is a dual cure type composition nor that it is prepared from two pastes.

Patent Document 1 Japanese Laid-Open Patent Publication No. Hei 11-335220

DISCLOSURE OF INVENTION

Problems to be Solved by Invention

The present inventor has evaluated commercially available dual cure type core build-up compositions of the two-paste type, resulting in finding that these compositions comprehensively have the following problems:

(1) Since two pastes have high viscosity, it is not easy to mix them;

(2) in mixing the two pastes, bubbles are easily formed in the resultant mixture; and (3) since the mixture of the two pastes has high viscosity, it is difficult to fill it in a tooth canal forming portion.

With respect to the problems (1) and (2), when the pastes are incompletely mixed or bubbles are present in the mixture, a built-up abutment (polymerically cured substance) is degraded in the mechanical strength. When a mixing device, which includes a pair of cylindrical containers arranged in parallel, a mixer provided at the front ends of the containers and an extruder composed of a pair of cylindrical extruding members respectively fit in the containers from the rear ends thereof and fixedly connected to each other, is used, the mixture can be discharged from the tip of the mixer merely by charging two pastes respectively in the two containers and performing an extruding operation. Although the problems (1) and (2) can be overcome or reduced by using such a device, since the pastes have high viscosity, a large extruding force is necessary.

Accordingly, the commercially available products of the dual cure type core build-up composition are desired to be further improved in the mixing property of the pastes and the filling property of the mixture. The present inventor has measured the viscosities of the aforementioned commercially available products of the dual cure type core build-up composition and found that the viscosities of the two pastes of "UniFil-Core" (manufactured by GC Corporation; trade name) are 550 P (poise) and 480 P, the viscosities of the two pastes of "LuxaCore-Dual" (manufactured by Dental-Material Gesselschaft mbH; trade name) are 650 P and 550 P, and the viscosities of the two pastes of "Build-it FR" (manufactured by Generic Pentron; trade name) are 750 P and 600 P. These viscosities are measured under the same conditions as those employed for measuring the viscosities of compositions according to this invention described below.

The viscosities of the commercially available products of the dual cure type core build-up compositions (pastes) are thus high because each composition includes a large amount of filler for improving the mechanical property of a polymerically cured substance to be formed. In order to lower the viscosity of each paste of the dual cure type core build-up composition with the large content of filler kept, it is presumed, for example, that the content of a monomer with a high viscosity such as bisphenol A diglycidyl (meth)acrylate should be reduced with the content of a dilution monomer with a low viscosity such as triethylene glycol di(meth)acrylate increased. However, the monomer with a high viscosity such as bisphenol A diglycidyl (meth)acrylate makes contribution in improving the mechanical property of the polymerically cured substance to be formed, and therefore, the reduction of this content leads to an opposite result to the aim of the large content of filler to improve the mechanical property.

Patent Document 1 proposes a viscosity of 3 through 300 P as a condition of the dental curable composition that can be applied in a small thickness with a small brush. However, the performance requirement of a core build-up material aimed by the present invention is completely different from the performance requirement of the application composition described in Patent Document 1, and therefore, this viscosity condition cannot be consultative. If the application composition described in Patent Document 1 is directly diverted to a core build-up material, it is generally difficult to build up an abutment because the flowability is too high to attain sufficient shape retention. It is noted that the viscosity described in Patent Document 1 is measured under different conditions from the viscosity of the compositions according to this invention and hence the relationship between these viscosities cannot be simply obtained.

The present invention was devised in consideration of the aforementioned circumstances, and an object of the invention is providing a divided type dental polymeric core build-up material exhibiting high operability in core build-up and capable of forming a polymerically cured substance having a good mechanical property.

Means for Solving Problems

In order to achieve the object, the divided type dental polymeric core build-up material according to Claim 1 of the invention includes a first paste (A) and a second paste (B), and each of the first paste (A) and the second paste (B) is a paste that includes a (meth)acrylate monomer (I), a filler (II) having a particle size distribution within a range of 0.1 through 40 μm and an average particle diameter of 0.7 through 10 μm, and a fine particle filler (III) having an average particle diameter of primary particles of 0.001 through 0.050 μm, and has a viscosity at 25° C. of 280 through 470 P, one of the first paste (A) and the second paste (B) includes an oxidant (IV) and the other includes a reductant (V), and at least one of the first paste (A) and the second paste (B) includes a photopolymerization catalyst (VI).

The divided type dental polymeric core build-up material according to Claim 2 of the invention includes a first paste (A) and a second paste (B), and each of the first paste (A) and the second paste (B) is a paste that is obtained by mixing at least a (meth)acrylate monomer (I), a filler (II) having a particle size distribution within a range of 0.1 through 40 μm and an average particle diameter of 0.7 through 10 μm, and a fine particle filler (III) having an average particle diameter of primary particles of 0.001 through 0.050 μm, and has a viscosity at 25° C. of 280 through 470 P, one of the first paste (A) and the second paste (B) includes an oxidant (IV) and the other includes a reductant (V), and at least one of the first paste (A) and the second paste (B) includes a photopolymerization catalyst (VI).

According to Claim 3 of the invention, the filler (II) of the divided type dental polymeric core build-up material according to Claim 2 has a particle size distribution within a range of 0.5 through 30 μm and an average particle diameter of 0.7 through 10 μm.

According to Claim 4 of the invention, the filler (II) of the divided type dental polymeric core build-up material according to Claim 2 has a particle size distribution within a range of 0.5 through 30 μm and an average particle diameter of 1.5 through 10 μm.

According to Claim 5 of the invention a mixture of the first paste (A) and the second paste (B) of the divided type dental polymeric core build-up material according to any of Claims 2 through 4 has a viscosity at 25° C. of 280 through 470 P.

According to Claim 6 of the invention, both of the first paste (A) and the second paste (B) of the divided type dental polymeric core build-up material according to any of Claims 2 through 5 include the photopolymerization catalyst (VI).

According to Claim 7 of the invention, in the divided type dental polymeric core build-up material according to Claim 6, ratios of the filler (II), the fine particle filler (III), the oxidant (IV) and the photopolymerization catalyst (VI) included in the first paste (A) are respectively 190 through 370 parts by weight, 3 through 60 parts by weight, 0.01 through 5 parts by weight and 0.01 through 5 parts by weight assuming that a ratio of the (meth)acrylate monomer (I) included in the first paste (A) is 100 parts by weight, and ratios of the filler (II), the fine particle filler (III), the reductant (V) and the photopolymerization catalyst (VI) included in the second paste (B) are respectively 190 through 370 parts by weight, 3 through 60 parts by weight, 0.01 through 5 parts by weight and 0.01 through 5 parts by weight assuming that a ratio of the (meth)acrylate monomer (I) included in the second paste (B) is 100 parts by weight.

According to Claim 8 of the invention, a weight ratio between the first paste (A) and the second paste (B) of the divided type dental polymeric core build-up material according to Claim 7 is 1:2 through 2:1.

Hereinafter, the divided type dental polymeric core build-up materials according to Claims 1 through 8 are sometimes generically designated as "the dental polymeric core build-up material of this invention".

EFFECTS OF INVENTION

The divided type dental polymeric core build-up material according to each of Claims 1 through 8 is restricted in the viscosities of the respective pastes and the particle diameter conditions of the filler (II) and the fine particle filler (III) included in each paste, so that it can be highly operable in core build-up and can form a polymerically cured substance having a good mechanical property.

The divided type dental polymeric core build-up material according to each of Claims 6 through 8 includes the photopolymerization catalyst (VI) in both the first paste (A) and the second paste (B), and therefore in addition to the aforementioned characteristics, it has characteristics that sensitivity to ambient light is high and a mixture obtained before curing minimally has mottling that can lower the esthetic property.

BEST MODE FOR CARRYING OUT INVENTION

The dental polymeric core build-up material of this invention is a divided type dental polymeric core build-up material including a first paste (A) and a second paste (B). The weight ratio between the first paste (A) and the second paste (B), which depends upon components of the pastes and their contents, is generally 1:2 through 2:1 and is preferably approximately 1:1 in many cases. Each of the pastes includes a (meth)acrylate monomer (I), a filler (II) having a particle size distribution within a range of 0.1 through 40 μm and an average particle diameter of 0.7 through 10 μm, and a fine particle filler (III) having an average particle diameter of primary particles of 0.001 through 0.050 μm. Herein the "(meth)acrylate monomer" is generically used for a methacrylate monomer and an acrylate monomer.

The (meth)acrylate monomer (I) included in each of the first paste (A) and the second paste (B) is not particularly specified as far as one or more acrylic groups or methacrylic groups are included as a polymeric group. Specific examples are described below dividedly as (i) monofunctional monomers having one polymeric group, (ii) bifunctional monomers having two polymeric groups and (iii) tri- or multi functional monomers having three or more polymeric groups.

(i) Monofunctional Monomers:

methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 3-(meth)acryloyloxypropyl trimethoxysilane, 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth)acrylate, propylene glycol mono(meth)acrylate, glycerin mono(meth)acrylate, erythritol mono(meth)acrylate, N-methylol (meth)acrylamide, N-hydroxyethyl (meth)acrylamide, N,N-bis(hydroxyethyl) (meth)acrylamide, (meth)acryloyloxydodecyl pyridinium bromide (ii) Bifunctional Monomers:

ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl (meth)acrylate, 2-hydroxy-3-(meth)acryloyloxypropyl (meth)acrylate, 2,2-bis[4-(meth)acryloyloxypolyethoxyphenyl]propane, 1,2-bis[3-(meth)acryloyloxy-2-hydroxypropyloxy]ethane, 2,15-dihydroxy-1,16-di(meth)acryloyloxy-4,7, 10,13-tetraoxahexadecane, 1,3-bis 3-(meth)acryloyloxy-2-hydroxypropyloxyl-2-propanol, pentaerythritol di(meth) acrylate, N,N'-(2,2,4-trimethylhexamethylene)-bis[2-(aminocarbonyloxy)ethane-1-ol] di(meth)acrylate Tri- or Multi Functional Monomers:

trimethylolpropane tri(meth)acrylate, trimethylolethane tri(meth)acrylate, tetramethylolmethane tri(meth)acrylate, pentaerythritol tetra(meth)acrylate, 1,7-diacryloyloxy-2,2,6, 6-tetraacryloyloxymethyl-4-oxyheptane, dipentaerythritol hexa(meth)acrylate One of these (meth)acrylate monomers (I) may be singly used or a plurality of them may be mixedly used. Also, the (meth)acrylate monomers (I) respectively included in the first paste (A) and the second paste (B) may be the same as or different from each other. As the (meth)acrylate monomer (I), a (meth)acrylate monomer including a phosphoric acid group, a carboxylic acid group, a pyrophosphoric acid group or a sulfonic acid group, which is generally known as a dental material, may be used. Furthermore, a polymer such as polymethyl (meth)acrylate or polyurethane may be used together with the (meth)acrylate monomer (I). Alternatively, the so-called macro monomer in which (meth)acryl groups are introduced to both ends of a polyaddition reaction product of diol and disocyanate (i.e., polyurethane) may be used instead of such a polymer.

Examples of the filler (II) and the fine particle filler (III) included in each paste are glass [including silicon dioxide (such as quartz, quartz glass or silica), alumina and silicon as a principal component and further including boron and/or aluminum together with various heavy metals such as lanthanum, barium and strontium], ceramic, kaolin, clay mineral (such as montmorillonite), mica, calcium fluoride, calcium phosphate, barium sulfate, zirconium oxide, titanium oxide and ytterbium fluoride. The shapes of the filler (II) and the fine particle filler (III) are not particularly specified and may be any shape including a crashed shape, a spherical shape and a specific shape. Such a filler is preferably used after a surface treatment with a known surface-treatment agent such as a silane coupling agent or a titanate coupling agent because the mixing property is thus improved. The filler (II) and the fine particle filler (III) included in the first paste (A) may be the same as or different from those included in the second paste (B).

The filler (II) included in each paste is a powder having a particle size distribution within a range of 0.1 through 40 μm and an average particle diameter of 0.7 through 10 μm, and a powder having a particle size distribution within a range of 0.5 through 30 μm and an average particle diameter of 0.7 through 10 μm is preferred and a powder having a particle size distribution within a range of 0.5 through 30 μm and an average particle diameter of 1.5 through 10 μm is more preferred. With respect to the particle size distribution and the average particle diameter of the filler (II), the filler is dispersed in a carrier medium to be used as a sample for obtaining particle size distribution data through a laser diffraction scattering method, and an average particle diameter can be calculated on the basis of the thus obtained data. It is noted that a particle size distribution within a range of 0.1 through 40 μm means that the thus obtained particle size distribution data substantially fall within an arbitrary region in a range of 0.1 through 40 μm.

Also, the fine particle filler (III) included in each paste is a fine particle powder having an average particle diameter of primary particles of 0.001 through 0.050 μm and preferably of 0.005 through 0.045 μm. The average particle diameter of primary particles of the fine particle filler (III) is an average value of particle diameters calculated on the basis of particle size distribution data obtained through image processing using a scanning electron microscope (SEM).

The two kinds of powders having largely different particle diameters are included in each paste in this invention because it is difficult to obtain, by single use of the filler (II) or the fine particle filler (III), a dental polymeric core build-up material having high operability in the core build-up, such as operability in extruding or mixing the pastes, and capable of forming a polymerically cured substance with a good mechanical property. Specifically, when the filler (II) is singly used, a resultant paste cannot keep its paste form and is in a highly flowable form, and hence, the filler (II) is easily precipitated with time. On the other hand, when the fine particle filler (III) is singly used, the viscosity of a resultant paste is increased even when its content is small, and hence, the flowability is lost and a resultant polymerically cured substance cannot attain a sufficient mechanical property.

A particle size distribution of the filler (II) out of the range of 0.1 through 40 μm is not preferable because it is difficult to simultaneously improve the operability of the paste attained in the core build-up and the mechanical property of the built-up abutment (the polymerically cured substance) in this case. A particle size distribution of the filler (II) within a range of 0.5 through 30 μm is particularly preferable because the operability of the paste and the mechanical property of the abutment can be both largely improved in this case. An average particle diameter of the filler (II) smaller than 0.7 μm is not preferable because the flowability of the paste is lost and the mechanical property is lowered in this case, and an average particle diameter larger than 10 μm is not preferable because the paste cannot keep its paste form and highly flowable in this case. In order to secure a good filling property of the paste, the average particle diameter of the filler (II) is particularly preferably 1.5 through 10 μm.

An average particle diameter of the primary particles of the fine particle filler (III) smaller than 0.001 μm is not preferable because the flowability of the paste attained in the core build-up is lowered in this case, and an average particle diameter larger than 0.050 μm is not preferable because the paste cannot keep its paste form and highly flowable in this case. In order to secure a good filling property of the paste, the average particle diameter of primary particles of the fine particle filler (III) is particularly preferably 0.005 through 0.045 μm.

For easily obtaining a desired viscosity of each paste ranging from 280 to 470 P, the content of the filler (II) in each paste is preferably 190 through 370 parts by weight and more preferably 200 through 320 parts by weight based on 100 parts by weight of the (meth)acrylate monomer (I) included in the paste. Also, for easily obtaining a desired viscosity of each paste ranging from 280 to 470 P, the content of the fine particle filler (III) in each paste is preferably 3 through 60 parts by weight and more preferably 10 through 40 parts by weight based on 100 parts by weight of the (meth)acrylate monomer (I) included in the paste. The contents of the filler (II) may be the same or different in the respective pastes. Also, the contents of the fine particle filler (III) may be the same or different in the respective pastes.

The dental polymeric core build-up material of this invention includes, as a chemical polymerization initiator, a redox catalyst composed of an oxidant (IV) and a reductant (V). The oxidant (IV) and the reductant (V) are dividedly included in the two pastes. This is for securing storage stability by preventing a redox reaction from occurring during the storage. With respect to each of the oxidant (IV) and the reductant (V), one kind may be singly used or a plurality of kinds may be used together.

Examples of the oxidant (IV) are organic peroxides such as benzoyl peroxide, ketone peroxide, peroxy ketal, diacyl peroxide, dialkyl peroxide, hydroperoxide, cumene hydroperoxide and silyl peroxide.

Examples of the reductant (V) are trimethylamine, tirpropylamine, tributylamine, trialylamine, ethyl diethanolamine, N,N-dimethyl-para-toluidine, N,N-dimethanol-para-toluidine, N,N-diethanol-para-toluidine, phenyl morpholine, N,N-bis(hydroxyethyl)xylidine and toluenesulfinic acid.

For easily obtaining a polymeric curing rate suitable to the core build-up operation and easily obtaining a good mechanical property of a built-up abutment, the content of the oxidant (IV) in one paste is preferably 0.01 through 5 parts by weight and more preferably 0.03 through 3 parts by weight based on 100 parts by weight of the (meth)acrylate monomer (I) included in the paste. Also, for easily obtaining a polymeric curing rate suitable to the core build-up operation and easily obtaining a good mechanical property of a built-up abutment, the content of the reductant (VI) in the other paste is preferably 0.01 through 5 parts by weight and more preferably 0.03 through 3 parts by weight based on 100 parts by weight of the (meth)acrylate monomer (I) included in the paste.

The dental polymeric core build-up material of this invention is a dual cure type material including not only the redox catalyst but also a photopolymerization catalyst (VI) in at least one paste. This is because the polymeric curing time cannot be easily adjusted by using the redox catalyst alone. One kind of or a plurality of kinds of photopolymerization catalyst (VI) may be used. In order to obtain a dental polymeric core build-up material having stability of pastes against ambient light and free from mottling of a mixture obtained before curing, the photopolymerization catalyst (VI) is preferably included in the both pastes. In this case, the photopolymerization catalyst (VI) included in the first paste (A) may be the same as or different from that included in the second paste (B).

A typical example of the photopolymerization catalyst (VI) is a combination of a photosensitizer such as α-diketone represented by camphor quinone and a photopolymerization promoter. Examples of the photopolymerization promoter used in this combination are tertiary amines such as N,N-dimethylaminoethyl methacrylate, N,N-dimethylaminobenzoic acid alkyl ester; barbituric acids such as 1-benzyl-5-phenyl barbituric acid; organic peroxides such as benzoyl peroxide; mercaptans such as mercaptobenzooxazole; azo compounds such as azobisisobutyronitrile; and aldehydes such as benzaldehyde. Alternatively, a UV polymerization initiator such as benzyldimethy ketal or benzoinisopropyl ether; or an acyl phosphine oxide-based photopolymerization initiator may be used as the photopolymerization catalyst (VI). Examples of the acyl phosphine oxide-based photopolymerization initiator are 2,4,6-trimethylbenzoyldiphenyl phosphine oxide, 2,6-dimethoxybenzoyldiphenyl phosphine oxide, 2,3,5,6-tetramethylbenzoyldiphenyl phosphine oxide, benzoylbis(2,6-dimethylphenyl) phosphonate and 2,4,6-trimethylbenzoylethoxyphenyl phosphine oxide. One of these acyl phosphine oxide-based photopolymerization initiators may be singly used or may be used together with a photopolymerization promoter such as amines, aldehydes or mercaptans.

In the case where the photopolymerization catalyst (VI) is included in the both pastes, for easily suppressing the influence, caused in the core build-up, of the ambient light on polymeric curing promotion so as not to disturb the build-up operation and for easily attaining a good mechanical property of a built-up abutment, the content of the photopolymerization catalyst (VI) in each paste is preferably 0.01 through 5 parts by weight and more preferably 0.03 through 3 parts by weight based on 100 parts by weight of the (meth)acrylate monomer (I) included in the paste. In the case where the photopolymerization catalyst (VI) is included in one of the pastes alone, for easily suppressing the influence, caused in the core build-up, of the ambient light on the polymeric curing promotion so as not to disturb the build-up operation and for easily attaining a good mechanical property of a built-up abutment, the content of the photopolymerization catalyst (VI) is preferably 0.02 through 10 parts by weight and more preferably 0.06 through 6 parts by weight based on 200 parts by weight of the (meth)acrylate monomer (I) included in the both pastes. When the photopolymerization catalyst (VI) is included in the both pastes, the contents of the photopolymerization catalyst (VI) may be the same or different in the respective pastes.

The viscosity at 25° C. of each paste is restricted to a range of 280 through 470 P (poise). The viscosities of the respective plates may be the same as or different from each other as far as they fall within the above-described range. When the viscosity is lower than 280 P, the flowability is so high that the filling property for a root canal of a tooth is high but the shape retention in an abutment with a core built up is poor. When the viscosity exceeds 470 P, to the contrary, the shape retention is good but the filling property is poor. Also, in the case where the viscosity of a mixture of the pastes at 25° C. attained immediately after mixing is 280 through 470 P, the filling property for a root canal of a tooth and the shape retention in an abutment with a core built up can be both attained at high level. It is noted that the viscosity is measured at 25° C. with a cone-plate type rotational viscometer.

The viscosity of each paste can be experimentally set to a desired value by properly selecting the kinds, the amounts, the sizes and the like of the (meth)acrylate monomer (I), the filler (II) and the fine particle filler (III). Also, the viscosity of the mixture of the pastes depends upon the viscosities of the respective pastes and generally falls within the range of 280 through 470 P as far as the viscosities of the respective pastes are both 280 through 470 P.

A suitable example of one paste includes bisphenol A diglycidyl (meth)acrylate [corresponding to the (meth)acrylate monomer (I) used for improving the mechanical property], triethylene glycol (meth)acrylate [corresponding to the (meth)acrylate monomer (I) used for lowering the viscosity], borosilicate glass [corresponding to the filler (II)], colloidal silica [corresponding to the fine particle filler (III)], benzoyl peroxide [corresponding to the oxidant (IV)], and camphor quinone and benzaldehyde [corresponding to the photopolymerization catalyst (VI)].

A suitable example of the other paste includes 2,2-bis[4-(meth)acryloyloxypolyethoxyphenyl]propane [corresponding to the (meth)acrylate monomer (I) used for improving the mechanical property], triethylene glycol di(meth)acrylate [corresponding to the (meth)acrylate monomer (I) used for lowering the viscosity], borosilicate glass [corresponding to the filler (II)], colloidal silica [corresponding to the fine particle filler (III)], N,N-diethanol-para-toluidine [corresponding to the reductant (V)], and camphor quinone and tertiary amine [corresponding to the photopolymerization catalyst (VI)].

Each of the first paste (A) and the second paste (B) is prepared by mixing the (meth)acrylate monomer (I), the filler (II), the fine particle filler (III), the redox catalyst component [the oxidant (IV) or the reductant (V)] and the photopolymerization catalyst (VI) with a mixer such as a stirrer, a kneader or a disperser. In the case where the photopolymerization catalyst (VI) is included in one of the pastes alone, the photopolymerization catalyst (VI) is not mixed in the other paste.

At least one of the pastes may include a UV absorber, an antioxidant, a polymerization inhibitor, a pigment, a dye and so on if necessary.

The dental polymeric core build-up material of this invention is a material for use in the core build-up in which the first paste (A) and the second paste (B) are dividedly packed (namely, contained in different vessels or packages) as described above. The first paste (A) and the second paste (B) are divided so as not to come into contact with each other, and in the core build-up, appropriate amounts of these pastes are taken out of the vessels or packages to be mixed with each other for use. The vessels or packages for containing the pastes are not particularly specified, and are preferably in an extrudable form such as a syringe or a tube in consideration of easiness in taking out the paste. Furthermore, in consideration of convenience in the core build-up operation, a particularly preferable form is a mixing device including a pair of cylindrical containers arranged in parallel, a mixer provided at the front ends of the containers and an extruder composed of a pair of cylindrical extruding members respectively fit in the containers from the rear ends thereof and fixedly connected to each other with the two pastes individually charged in the respective containers. In consideration of the storage property for a long period of time, the vessels or packages preferably have a high light blocking property and a high sealing property so that the pastes contained therein can be shut off from ambient light and oxygen.

EMBODIMENTS

The present invention will now be more specifically described on the basis of preferred embodiments thereof, and it is noted that the invention is not limited to the following embodiments. Abbreviations used in description below stand for the following:

Bis-GMA: bisphenol A diglycidyl methacrylate
Bis-MEPP: 2,2-bis[4-methacryloyloxypolyethoxyphenyl]propane
3G: triethylene glycol dimethacrylate
BPO: benzoyl peroxide (oxidant)
DEPT: N,N-diethanol-para-toluidine (reductant)
CQ: dl-camphor quinone (photopolymerization catalyst)
OBA: p-n-octylbenzaldehyde (photopolymerization catalyst)
DMA: ethyl 4-(N,N-dimethylamino)benzoate (photopolymerization catalyst)

Embodiment 1

A first paste and a second paste were prepared by methods described below, so as to fabricate a divided type dental polymeric core build-up material including these pastes in a weight ratio of 1:1.

<First Paste>

After dispersing 420 parts by weight of a crushed glass filler (glass filler: manufactured by Schott AG, trade code "8235") in water contained in a constant temperature water bath kept at 30° C. with an agitating blade and allowing the resultant to stand for 6 hours, a portion of the dispersed filler included in a supernatant and not precipitated was removed, so as to give a precipitated glass filler having a particle size distribution within a range of 0.7 through 27 μm and an average particle diameter of 4.5 μm. Subsequently, 4 parts by weight of 3-methacryloyloxypropyl trimethoxysilane was dispersed in water contained in a constant temperature water bath kept at 30° C. with an agitating blade, and hydrolysis was caused with a slight amount of acetic acid added thereto, and thereafter, 272 parts by weight of the precipitated glass filler was dispersed therein for a surface treatment, so as to prepare a filler. Also, 4.5 parts by weight of 3-methacryloyloxypropyl trimethoxysilane was dispersed in water contained in a constant temperature water bath kept at 30° C. with an agitating blade, and hydrolysis was caused with a slight amount of acetic acid added thereto, and thereafter, 28 parts by weight of colloidal silica with an average particle diameter of 0.040 μm was dispersed therein for a surface treatment, so as to prepare a fine particle filler. Then, 60 parts by weight of Bis-GMA, 40 parts by weight of 3 G, 1.5 parts by weight of BPO, 1.5 parts by weight of CQ and 1.5 parts by weight of OBA were mixed to prepare a solution, and 272 parts by weight of the filler and 28 parts by weight of the fine particle filler were added to the solution. The resultant was mixed with a versatile mixer (manufactured by Dalton Co., Ltd.), thereby preparing the first paste (first paste (A).

<Second Paste>

After dispersing 2.5 parts by weight of 3-methacryloyloxypropyl trimethoxysilane in water contained in a constant temperature water bath kept at 30° C. with an agitating blade and causing hydrolysis with a slight amount of acetic acid added thereto, 248 parts by weight of a crushed glass filler (glass filler: manufactured by Esstec Inc., trade code "#3000") having a particle size distribution within a range of 0.6 through 21 μm and an average particle diameter of 2.5 μm was dispersed therein for a surface treatment, so as to prepare a filler. Then, 90 parts by weight of Bis-MEPP, 10 parts by weight of 3 G, 1.7 parts by weight of DEPT, 0.6 part by weight of CQ and 2.0 parts by weight of DMA were mixed to prepare a solution, and 248 parts by weight of the filler and 22 parts by weight of the same fine particle filler as that used in the first paste were added to the solution. The resultant was mixed with a versatile mixer (manufactured by Dalton Co., Ltd.), thereby preparing the second paste (second paste (B)).

Embodiment 2

A first paste and a second paste were prepared by methods described below, so as to fabricate a divided type dental polymeric core build-up material including these pastes in a weight ratio of 1:1.
<First Paste>
The first paste (first paste (A)) was prepared in the same manner as the first paste of Embodiment 1 except that the ratios of the filler and the fine particle filler were respectively changed to 236 parts by weight and 21 parts by weight.
<Second Paste>
The second paste (second paste (B)) was prepared in the same manner as the second paste of Embodiment 1 except that the ratios of the filler and the fine particle filler were respectively changed to 217 parts by weight and 17 parts by weight.

Embodiment 3

A first paste and a second paste were prepared by methods described below, so as to fabricate a divided type dental polymeric core build-up material including these pastes in a weight ratio of 1:1.
<First Paste>
The first paste (first paste (A)) was prepared in the same manner as the first paste of Embodiment 1 except that the ratios of the filler and the fine particle filler were respectively changed to 318 parts by weight and 36 parts by weight.
<Second Paste>
The second paste (second paste (B)) was prepared in the same manner as the second paste of Embodiment 1 except that the ratios of the filler and the fine particle filler were respectively changed to 288 parts by weight and 29 parts by weight.

Embodiment 4

A first paste and a second paste were prepared by methods described below, so as to fabricate a divided type dental polymeric core build-up material including these pastes in a weight ratio of 1:1.
<First Paste>
The first paste (first paste (A)) was prepared in the same manner as the first paste of Embodiment 1 except that the ratio of the CQ was changed to 2.1 parts by weight.
<Second Paste>
The second paste (second paste (B)) was prepared in the same manner as the second paste of Embodiment 1 except that neither the CQ nor the DMA was included.

Embodiment 5

A first paste and a second paste were prepared by methods described below so as to fabricate a divided type dental polymeric core build-up material including these pastes in a weight ratio of 1:1.
<First Paste>
The first paste (first paste (A)) was prepared in the same manner as the first paste of Embodiment 1 except that neither the CQ nor the OBA was included.
<Second Paste>
The second paste (second paste (B)) was prepared in the same manner as the second paste of Embodiment 1 except that the ratio of the CQ was changed to 2.1 parts by weight.

Embodiment 6

A first paste and a second paste were prepared by methods described below, so as to fabricate a divided type dental polymeric core build-up material including these pastes in a weight ratio of 1:1.
<First Paste>
A surface-treated filler was prepared in the same manner as in the preparation method for the filler described with respect to the second paste of Embodiment 1 except that 248 parts by weight of the crushed glass filler having a particle size distribution within a range of 0.6 through 21 μm and an average particle diameter of 2.5 μm was replaced with 240 parts by weight of a crushed glass filler having a particle size distribution within a range of 0.5 through 6 μm and an average particle diameter of 1.5 μm and that the ratio of the 3-methacryloyloxypropyl trimethoxysilane was changed from 2.5 parts by weight to 4.8 parts by weight. The first paste (first paste (A)) was prepared in the same manner as the first paste of Embodiment 1 except that this filler was used (in a ratio of 240 parts by weight).
<Second Paste>
A surface-treated filler was prepared in the same manner as in the preparation method for the filler described with respect to the second paste of Embodiment 1 except that 248 parts by weight of the crushed glass filler having a particle size distribution within a range of 0.6 through 21 μm and an average particle diameter of 2.5 μm was replaced with 220 parts by weight of a crushed glass filler having a particle size distribution within a range of 0.5 through 6 μm and an average particle diameter of 1.5 μm and that the ratio of the 3-methacryloyloxypropyl trimethoxysilane was changed from 2.5 parts by weight to 4.8 parts by weight. The second paste (second paste (B)) was prepared in the same manner as the second paste of Embodiment 1 except that this filler was used (in a ratio of 220 parts by weight).

Embodiment 7

A first paste and a second paste were prepared by methods described below, so as to fabricate a divided type dental polymeric core build-up material including these pastes in a weight ratio of 1:1.
<First Paste>
A surface-treated filler was prepared in the same manner as in the preparation method for the filler described with respect to the second paste of Embodiment 1 except that 248 parts by weight of the crushed glass filler having a particle size distribution within a range of 0.6 through 21 μm and an average particle diameter of 2.5 μm was replaced with 200 parts by weight of a crushed glass filler having a particle size distribution within a range of 0.3 through 4 μm and an average particle diameter of 1.0 μm and that the ratio of the 3-methacryloyloxypropyl trimethoxysilane was changed from 2.5 parts by weight to 6.0 parts by weight. The first paste (first paste (A)) was prepared in the same manner as the first paste of Embodiment 1 except that this filler was used (in a ratio of 200 parts by weight).

<Second Paste>

A surface-treated filler was prepared in the same manner as in the preparation method for the filler described with respect to the second paste of Embodiment 1 except that 248 parts by weight of the crushed glass filler having a particle size distribution within a range of 0.6 through 21 µm and an average particle diameter of 2.5 µm was replaced with 200 parts by weight of a crushed glass filler having a particle size distribution within a range of 0.3 through 4 µm and an average particle diameter of 1.0 µm and that the ratio of the 3-methacryloyloxypropyl trimethoxysilane was changed from 2.5 parts by weight to 6.0 parts by weight. The second paste (second paste (B)) was prepared in the same manner as the second paste of Embodiment 1 except that this filler was used (in a ratio of 200 parts by weight).

Embodiment 8

A first paste and a second paste were prepared by methods described below, so as to fabricate a divided type dental polymeric core build-up material including these pastes in a weight ratio of 1:1.

<First Paste>

A surface-treated filler was prepared in the same manner as in the preparation method for the filler described with respect to the second paste of Embodiment 1 except that 248 parts by weight of the crushed glass filler having a particle size distribution within a range of 0.6 through 21 µm and an average particle diameter of 2.5 µm was replaced with 350 parts by weight of a crushed glass filer having a particle size distribution within a range of 1 through 40 µm and an average particle diameter of 8.0 µm and that the ratio of the 3-methacryloyloxypropyl trimethoxysilane was changed from 2.5 parts by weight to 3.5 parts by weight. The first paste (first paste (A)) was prepared in the same manner as the first paste of Embodiment 1 except that this filler was used (in a ratio of 350 parts by weight).

<Second Paste>

A surface-treated filler was prepared in the same manner as in the preparation method for the filler described with respect to the second paste of Embodiment 1 except that 248 parts by weight of the crushed glass filler having a particle size distribution within a range of 0.6 through 21 µm and an average particle diameter of 2.5 µm was replaced with 350 parts by weight of a crushed glass filler having a particle size distribution within a range of 1 through 40 µm and an average particle diameter of 8.0 µm and that the ratio of the 3-methacryloyloxypropyl trimethoxysilane was changed from 2.5 parts by weight to 3.5 parts by weight. The second paste (second paste (B)) was prepared in the same manner as the second paste of Embodiment 1 except that this filler was used (in a ratio of 350 parts by weight).

Embodiment 9

A first paste and a second paste were prepared by methods described below so as to fabricate a divided type dental polymeric core build-up material including these pastes in a weight ratio of 1:1.

<First Paste>

A surface-treated fine particle filler was prepared in the same manner as in the preparation method for the fine particle filler described with respect to the first paste of Embodiment 1 except that 28 parts by weight of the colloidal silica having an average particle diameter of 0.040 µm was replaced with 8 parts by weight of colloidal silica having an average particle diameter of 0.007 µm and that the ratio of the 3-methacryloxypropyl trimethoxysilane was changed from 4.5 parts by weight to 8.0 parts by weight. The first paste (first paste (A)) was prepared in the same manner as the first paste of Embodiment 1 except that this fine particle filler was used (in a ratio of 8 parts by weight).

<Second Paste>

A surface-treated fine particle filler was prepared in the same manner as in the preparation method for the fine particle filler described with respect to the first paste of Embodiment 1 except that 28 parts by weight of the colloidal silica having an average particle diameter of 0.040 µm was replaced with 8 parts by weight of colloidal silica having an average particle diameter of 0.007 µm and that the ratio of the 3-methacryloyloxypropyl trimethoxysilane was changed from 4.5 parts by weight to 8.0 parts by weight. The second paste (second paste (B)) was prepared in the same manner as the second paste of Embodiment 1 except that this fine particle filler was used (in a ratio of 8 parts by weight).

Comparative Example 1

A first paste and a second paste were prepared by methods described below, so as to fabricate a divided type dental polymeric core build-up material including these pastes in a weight ratio of 1:1.

<First Paste>

The first paste was prepared in the same manner as the first paste of Embodiment 1 except that the ratios of the filler and the fine particle filler were respectively changed to 206 parts by weight and 16 parts by weight.

<Second Paste>

The second paste was prepared in the same manner as the second paste of Embodiment 1 except that the ratios of the filler and the fine particle filler were respectively changed to 180 parts by weight and 12 parts by weight.

Comparative Example 2

A first paste and a second paste were prepared by methods described below so as to fabricate a divided type dental polymeric core build-up material including these pastes in a weight ratio of 1:1.

<First Paste>

The first paste was prepared in the same manner as the first paste of Embodiment 1 except that the ratios of the filler and the fine particle filler were respectively changed to 308 parts by weight and 47 parts by weight.

<Second Paste>

The second paste was prepared in the same manner as the second paste of Embodiment 1 except that the ratios of the filler and the fine particle filler were respectively changed to 338 parts by weight and 38 parts by weight.

Comparative Example 3

A first paste and a second paste were prepared by methods described below, so as to fabricate a divided type dental polymeric core build-up material including these pastes in a weight ratio of 1:1.

<First Paste>

The first paste was prepared in the same manner as the first paste of Embodiment 1 except that neither the CQ nor the OBA was included.

<Second Paste>

The second paste was prepared in the same manner as the second paste of Embodiment 1 except that neither the CQ nor the DMA was included.

Comparative Example 4

A first paste and a second paste were prepared by methods described below, so as to fabricate a divided type dental polymeric core build-up material including these pastes in a weight ratio of 1:1.

<First Paste>

A surface-treated filler was prepared in the same manner as in the preparation method for the filler described with respect to the second paste of Embodiment 1 except that 248 parts by weight of the crushed glass filler having a particle size distribution within a range of 0.6 through 21 μm and an average particle diameter of 2.5 μm was replaced with 190 parts by weight of a crushed glass filler having a particle size distribution within a range of 0.2 through 3 μm and an average particle diameter of 0.4 μm and that the ratio of the 3-methacryloyloxypropyl trimethoxysilane was changed from 2.5 parts by weight to 15.2 parts by weight. The first paste was prepared in the same manner as the first paste of Embodiment 1 except that this filler was used (in a ratio of 190 parts by weight).

<Second Paste>

A surface-treated filler was prepared in the same manner as in the preparation method for the filler described with respect to the second paste of Embodiment 1 except that 248 parts by weight of the crushed glass filler having a particle size distribution within a range of 0.6 through 21 μm and an average particle diameter of 2.5 μm was replaced with 190 parts by weight of a crushed glass filler having a particle size distribution within a range of 0.2 through 3 μm and an average particle diameter of 2.5 μm and that the ratio of the 3-methacryloyloxypropyl trimethoxysilane was changed from 2.5 parts by weight to 15.2 parts by weight. The second paste was prepared in the same manner as the second paste of Embodiment 1 except that this filler was used (in a ratio of 190 parts by weight).

Comparative Example 5

A first paste and a second paste were prepared by methods described below, so as to fabricate a divided type dental polymeric core build-up material including these pastes in a weight ratio of 1:1.

<First Paste>

A surface-treated filler was prepared in the same manner as in the preparation method for the filler described with respect to the first paste of Embodiment 1 except that 272 parts by weight of the precipitated glass filler having a particle size distribution within a range of 0.7 through 27 μm and an average particle diameter of 4.5 μm was replaced with 370 parts by weight of a precipitated glass filler having a particle size distribution within a range of 1 through 40 μm and an average particle diameter of 15.0 μm and that the ratio of the 3-methacryloyloxypropyl trimethoxysilane was changed from 4 parts by weight to 3.7 parts by weight. The first paste was prepared in the same manner as the first paste of Embodiment 1 except that this filler was used (in a ratio of 370 parts by weight).

<Second Paste>

A surface-treated filler was prepared in the same manner as in the preparation method for the filler described with respect to the second paste of Embodiment 1 except that 272 parts by weight of the precipitated glass filler having a particle size distribution within a range of 0.7 through 27 μm and an average particle diameter of 4.5 μm was replaced with 370 parts by weight of a crushed glass filler having a particle size distribution within a range of 1 through 40 μm and an average particle diameter of 15.0 μm and that the ratio of the 3-methacryloyloxypropyl trimethoxysilane was changed from 4 parts by weight to 3.7 parts by weight. The second paste was prepared in the same manner as the second paste of Embodiment 1 except that this filler was used (in a ratio of 370 parts by weight)

Comparative Example 6

A first paste and a second paste were prepared by methods described below, so as to fabricate a divided type dental polymeric core build-up material including these pastes in a weight ratio of 1:1.

<First Paste>

The first paste was prepared in the same manner as the first paste of Embodiment 1 except that the ratios of the filler and the fine particle filler were respectively changed to 450 parts by weight and 0 part by weight.

<Second Paste>

The second paste was prepared in the same manner as the second paste of Embodiment 1 except that the ratios of the filler and the fine particle filler were respectively changed to 450 parts by weight and 0 part by weight.

Comparative Example 7

A first paste and a second paste were prepared by methods described below, so as to fabricate a divided type dental polymeric core build-up material including these pastes in a weight ratio of 1:1.

<First Paste>

A surface-treated filler was prepared in the same manner as in the preparation method for the filler described with respect to the first paste of Embodiment 1 except that 272 parts by weight of the precipitated glass filler having a particle size distribution within a range of 0.7 through 27 μm and an average particle diameter of 4.5 μm was replaced with 400 parts by weight of a precipitated glass filler having a particle size distribution within a range of 1.0 through 60 μm and an average particle diameter of 8.0 μm. The first paste was prepared in the same manner as the first paste of Embodiment 1 except that this filler was used (in a ratio of 400 parts by weight).

<Second Paste>

A surface-treated filler was prepared in the same manner as in the preparation method for the filler described with respect to the first paste of Embodiment 1 except that 272 parts by weight of the precipitated glass filler having a particle size distribution within a range of 0.7 through 27 μm and an average particle diameter of 4.5 μm was replaced with 400 parts by weight of a precipitated glass filler having a particle size distribution within a range of 1.0 through 60 μm and an average particle diameter of 8.0 μm. The second paste was prepared in the same manner as the second paste of Embodiment 1 except that this filler was used (in a ratio of 400 parts by weight).

Each of the divided type dental polymeric core build-up materials prepared in Embodiments 1 through 9 and Comparative Examples 1 through 7 was examined for the ratios of the used components, the particle size distribution and the average particle diameter of the used filler, the average particle diameter of the used fine particle filler, the viscosity of each of the prepared pastes, and various properties and performances of the fabricated dental polymeric core build-up material [such as the viscosity, the extruding force (extruding property), the filling property, the mottling of a mixture obtained before curing, the sensitivity to the ambient light, and the flexural strength and the flexural modulus of a polymerically cured substance] by methods described below. The compositions and the evaluation results of the respective embodiments are listed in Tables 1 and 2 below, and the compositions and the evaluation results of the comparative examples are listed in Tables 3 and 4 below.

[Particle Size Distribution and Average Particle Diameter of Filler]

A suspension was prepared by placing 0.2 g of the filler and 20 mL of ethyl alcohol in a glass sample bottle and subjecting the resultant to a dispersing treatment for 20 minutes by using a ultrasonic homogenizer (manufactured by Branson, trade name "BRANSONIC"). The thus obtained suspension was used for obtaining the particle size distribution and the average particle diameter with a laser diffraction particle size analyzer (manufactured by Shimadzu Corporation, trade name "SALD-2100"). In each of the embodiments and the comparative examples, "standard refractive index (1)" (1.70-0.20 i) specified as a standard condition in the used particle size analyzer was employed as a "refractive index parameter" to be set as one of measurement conditions in the particle size analyzer, and when another filler is to be measured, the refractive index parameter may be appropriately changed in accordance with the kind of filler and so on.

[Average Particle Diameter of Primary Particles of Fine Particle Filler]

A photograph of the fine particle filler obtained by a scanning electron a microscope (manufactured by Hitachi High-Tech Science Systems Corporation, S-3500N) was observed, so as to obtain data of particle diameters and particle number by measuring particle diameters of individual particles observed in the visual field. A mean volume diameter of the particles was obtained in accordance with the equation for the Sauta mean diameter, and the thus calculated diameter was defined as the average particle diameter.

[Viscosities of Respective Pastes and Core Build-Up Material]

A plastic cylindrical vessel with an inner diameter of 9.5 mm charged with 0.6 ml of each paste was placed at the center of a cup disposed on a measuring part kept at 25° C. of a cone-plate type rotational viscometer (manufactured by Toki Sangyo Co, Ltd., E-type viscometer) so as to be rotated at a rotational speed of 0.5 rpm for 2 minutes immediately after closing the cover of the measuring part, and thereafter, the rotation was stopped to read a measured value, which was used to calculate the viscosity (P) in accordance with a conversion formula. This test was carried out three times, and an average of the three calculated values was defined as the viscosity. The viscosity measurement was performed at room temperature of 25° C. However, with respect to the core build-up material obtained by mixing the pastes, in order to eliminate the influence of viscosity increase caused with time by chemical polymerization, a mixture obtained immediately after mixing the pastes with no oxidant included in the first paste was used for measuring the viscosity, and the thus obtained viscosity of the mixture was defined as an alternate value of the viscosity of the core build-up material attained immediately after mixing the pastes.

[Extruding Force (Extruding Property)]

In measuring the extruding force, a mixing device including a pair of cylindrical polyolefin containers (with an internal volume of 5 ml, manufactured by MIXP-AC SYSTEMS AG, trade code "SDL-010-01-13(V01)") arranged in parallel, a mixer provided at the front ends of the containers and an extruder (manufactured by MIXPAC SYSTEMS AG, trade code "PLH010-01-46") composed of a pair of cylindrical extruding members respectively fit in the containers from the rear ends thereof and fixedly connected to each other was used. The mixer includes a mixing part (manufactured by MIXPAC SYSTEMS AG, trade code "ML-2.5-08-D") having 8 agitating blades (elements) and a plastic discharging part (manufactured by MIXPAC SYSTEMS AG, trade code "IOT212-20") provided at the tip of the mixing part and bent at an angle of 60 degrees, and the wall of the mixer was made of a member with an ambient light transmitting property.

After charging the first paste and the second paste respectively in the containers, the pair of extruding members were made to enter the pair of containers, so as to extrude the pastes contained in the containers into the mixing part, and the two pastes were mixed in the mixing part so that the thus obtained mixture could be discharged from the discharging part. The viscosity of this mixture was obtained by the aforementioned viscosity measuring method, and an extruding force (a force necessary for extruding the paste from the container into the mixer) was measured with a universal materials testing machine (manufactured by Shimadzu Corporation, trade code "AGI-100"). A test in which the paste was extruded with a load applied in the same manner as in a compressive strength test performed with a cross head speed set to 20 mm/min. for measuring the maximum load was performed three times, and an average of the thus obtained three measured values was defined as the extruding force. The maximum load was measured at room temperature of 25° C. An extruding force of 200 N or less was evaluated as "a" corresponding to a good extruding property, an extruding force of 250 N or more was evaluated as "c" corresponding to a poor extruding property, and an intermediate therebetween was evaluated as "b" corresponding to an ordinary extruding property.

[Filling Property]

The mixture was discharged by using the aforementioned mixing device into a hole with a diameter of 2 mm and a depth of 7 mm previously formed (correspondingly to a portion where a root canal of an abutment tooth was to be formed) in a plastic model of an abutment tooth (manufactured by Nissin Dental Product Inc., trade code "A50-438"), so as to examine the filling property. A mixture that could be filled down to the lowermost portion of the hole was evaluated as "a" corresponding to a good filling property, and a mixture that could not be filled down to the lowermost portion or a mixture having bubbles when filled was evaluated as "b" corresponding to a poor filling property.

[Slump Property]

With a circle having a diameter of 5 mm previously drawn on a glass plate in a square shape of 30 mm×30 mm, 0.06 g of the mixture was discharged within the circle by using the same mixing device as that used in the aforementioned evaluation of the extruding force, and the resultant glass plate was made to stand vertically in an incubator at 37° C. and allowed to stand for 30 seconds, so as to measure a distance by which the mixture moved from the circle. This test was performed three times, and an average of the three measured values was defined as a flow score (mm). A larger flow score means that the mixture can more easily flow. When a flow score obtained in this test is as long as 3 mm or more, such a mixture cannot be suitably used as a core build-up paste.

[Mottling of Mixture Obtained Before Curing]

An appropriate amount of mixture was discharged onto a glass plate in a square shape of 30 mm×30 mm by using the same mixing device as that used in the aforementioned evaluation of the extruding force, the mixture was sandwiched between two spacer plates (manufactured by Mitutoyo Corporation, trade name "gauge block") each having a thickness of 0.25 mm for restricting the thickness of the mixture reached when pressed, and then, another glass plate in a square shape of 30 mm×30 mm was placed on and pressed against the mixture so as to spread the mixture. The thus spread mixture was visually observed, and when the color was uniform, the mixture was evaluated as "a", when slight mottling was observed, the mixture was evaluated as "b", and when large mottling was observed, the mixture was evaluated as "c".

[Sensitivity to Ambient Light]

The same mixing device as that used in the evaluation of the extruding force was placed on a base, and the height of the base was adjusted so that the illuminance obtained by a dental light (manufactured by Morita Corporation, trade name "Operating Light LUNA-VUE") on the mixer of the mixing device could be 10000 lux. Subsequently, the dental light was switched on for irradiating the mixer, and simultaneously, 0.25 g of the first paste and 0.25 g of the second paste were extruded from the respective containers into the mixer over approximately 2 seconds so that the mixer could be filled with the paste mixture. Sixty seconds after starting extruding, the irradiation with the dental light was stopped, and the extruding operation was performed again, so as to check the flowability of the paste mixture contained in the mixer. In the case where it was difficult to extrude the mixture again because the mixture was photopolymerically cured within the mixer, the mixer was exchanged with another mixer of the same type, and a similar test was repeated in the same manner except that the light irradiation time was reduced from 60 seconds to 50 seconds. In this manner, the test was started with the irradiation time set to 60 seconds and was repeated similarly with the irradiation time reduced by 10 seconds each time until the flowability of the mixture could be confirmed by extruding it again. Assuming that the irradiation time employed in the test where the flowability was confirmed was T seconds, the test was performed in the same manner except that the irradiation time was set to (T+5) seconds. When the flowability was thus confirmed by extruding the mixture again, the evaluation result was recorded as (T+10) seconds. On the other hand, when the flowability could not be confirmed in the test with the irradiation time set to (T+5) seconds, the evaluation result was recorded as (T+5) seconds. As the recorded time is longer, the sensitivity to the ambient light is higher. It is noted that the divided type dental polymeric core build-up material of Comparative Example 3 in which none of the pastes included a photopolymerization initiator was not subjected to this test because it does not have function to start photopolymerization.

[Flexural Strength and Flexural Modulus of Polymerically Cured Substance]

Samples were fabricated and measurement was performed with reference to preparation of test specimens and testing procedure of Classes 2 and 3 according to 7.11.2.2. of ISO4049 (2000). First, a polyester film was placed on a slide glass, and a stainless steel frame with a width of 2 mm, a length of 25 mm and a depth of 2 mm was placed thereon. Subsequently, the mixture of the first paste and the second paste was filled within the frame, and the surface of the mixture contained within the frame was pressed with the slide glass with the polyester film sandwiched therebetween. Then, the mixture was irradiated for 40 seconds with a dental visible light irradiator (manufactured by Gunma Ushio Electric Inc., trade name "Lightel 2") while successively moving the irradiation window in parallel by a length corresponding to its radius, thereby obtaining a polymerically cured substance. The mixture within the frame was irradiated on its upper face and its lower face for forming the polymerically cured substance. Subsequently, the frame containing the polymerically cured substance was immersed in water kept at 37° C. for 15 minutes and was taken out of the water and then, the polymerically cured substance was taken out of the frame. The resultant polymerically cured substance was immersed in distilled water at 37° C. for 24 hours and then was subjected to a bending test. The flexural strength and the flexural modulus were measured through a three-point bend test performed by using a universal testing machine with a span set to 20 mm and a cross head speed set to 1 mm/min. An average value of flexural strength or flexural moduli obtained in five samples was defined as the flexural strength or the flexural modulus of the samples.

TABLE 1

| | | | Emb. 1 | Emb. 2 | Emb. 3 | Emb. 4 | Emb. 5 | Emb. 6 | Emb 7 | Emb. 8 | Emb. 9 |
|---|---|---|---|---|---|---|---|---|---|---|---|
| First paste | (Meth)acrylate monomer | Bis-GMA (parts by weight) | 60 | 60 | 60 | 60 | 60 | 60 | 60 | 60 | 60 |
| | | 3G (parts by weight) | 40 | 40 | 40 | 40 | 40 | 40 | 40 | 40 | 40 |
| | Filler (parts by weight) | | 272 | 236 | 318 | 272 | 272 | 240 | 200 | 350 | 272 |
| | Particle size distribution of filler (μm) | | 0.7-27 | 0.7-27 | 0.7-27 | 0.7-27 | 0.7-27 | 0.5-6 | 0.3-4 | 1-40 | 0.7-27 |
| | Average particle diameter of filler (μm) | | 4.5 | 4.5 | 4.5 | 4.5 | 4.5 | 1.5 | 1.0 | 8.0 | 4.5 |
| | Fine particle filler (parts by weight) | | 28 | 21 | 36 | 28 | 28 | 28 | 28 | 28 | 8 |
| | Averge particle diameter of fine particle filler (μm) | | 0.040 | 0.040 | 0.040 | 0.040 | 0.040 | 0.040 | 0.040 | 0.040 | 0.007 |
| | Oxidant | BPO (parts by weight) | 1.5 | 1.5 | 1.5 | 1.5 | 1.5 | 1.5 | 1.5 | 1.5 | 1.5 |
| | Photopolymerization catalyst | CQ/OBA (parts by weight) | 1.5/1.5 | 1.5/1.5 | 1.5/1.5 | 2.1/1.5 | 0/0 | 1.5/1.5 | 1.5/1.5 | 1.5/1.5 | 1.5/1.5 |
| | Viscosity (P): 25° C. | | 420 | 370 | 470 | 420 | 420 | 430 | 440 | 430 | 400 |
| Second paste | (Meth)acrylate monomer | Bis-MEPP (parts by weight) | 90 | 90 | 90 | 90 | 90 | 90 | 90 | 90 | 90 |
| | | 3G (parts by weight) | 10 | 10 | 10 | 10 | 10 | 10 | 10 | 10 | 10 |
| | Filler (parts by weight) | | 248 | 217 | 288 | 248 | 248 | 220 | 200 | 350 | 248 |
| | Particle size distribution of filler (μm) | | 0.6-21 | 0.6-21 | 0.6-21 | 0.6-21 | 0.6-21 | 0.5-6 | 0.3-4 | 1-40 | 0.6-21 |
| | Average particle diameter of filler (μm) | | 2.5 | 2.5 | 2.5 | 2.5 | 2.5 | 1.5 | 1.0 | 8.0 | 2.5 |
| | Fine particle filler (parts by weight) | | 22 | 17 | 29 | 22 | 22 | 22 | 22 | 22 | 8 |
| | Averge particle diameter of fine particle filler (μm) | | 0.040 | 0.040 | 0.040 | 0.040 | 0.040 | 0.040 | 0.040 | 0.040 | 0.007 |
| | Reductant | DEPT (parts by weight) | 1.7 | 1.7 | 1.7 | 1.7 | 1.7 | 1.7 | 1.7 | 1.7 | 1.7 |

TABLE 1-continued

|  |  | Emb. 1 | Emb. 2 | Emb. 3 | Emb. 4 | Emb. 5 | Emb. 6 | Emb 7 | Emb. 8 | Emb. 9 |
|---|---|---|---|---|---|---|---|---|---|---|
| Photopolymerization catalyst | CQ/DMA (parts by weight) | 0.6/2.0 | 0.6/2.0 | 0.6/2.0 | 0/0 | 2.1/2.0 | 0.6/2.0 | 0.6/2.0 | 0.6/2.0 | 0.6/2.0 |
| Viscosity (P): 25° C. |  | 330 | 280 | 380 | 330 | 330 | 330 | 420 | 370 | 350 |

TABLE 2

| Evaluation results | Embodiment 1 | Embodiment 2 | Embodiment 3 | Embodiment 4 | Embodiment 5 | Embodiment 6 | Embodiment 7 | Embodiment 8 | Embodiment 9 |
|---|---|---|---|---|---|---|---|---|---|
| Viscosity of mixture (P): 25° C. | 380 | 330 | 420 | 380 | 380 | 380 | 430 | 400 | 380 |
| Extruding force (N) | 105 | 80 | 200 | 116 | 121 | 110 | 240 | 120 | 115 |
| Extruding property | a | a | a | a | a | a | b | a | a |
| Filling property for root canal | a | a | a | a | a | a | a | a | a |
| Flow score (mm) | 0 | 0.1 | 0 | 0 | 0 | 0.1 | 0 | 0.2 | 0 |
| Mottling of mixture before curing | a | a | a | c | c | a | a | a | A |
| Sensitivity to ambient light (sec.) | 40 | 40 | 40 | 10 | 10 | 45 | 40 | 45 | 40 |
| Flexural strength (MPa) | 152 | 135 | 165 | 132 | 136 | 149 | 121 | 158 | 156 |
| Flexural modulus (GPa) | 13 | 11 | 14 | 11 | 11 | 11 | 10 | 13 | 11 |

TABLE 3

|  |  |  | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|---|---|
| First paste | (Meth)acrylate monomer | Bis-GMA (parts by weight) | 60 | 60 | 60 | 60 | 60 | 60 | 60 |
|  |  | 3G (parts by weight) | 40 | 40 | 40 | 40 | 40 | 40 | 40 |
|  | Filler (parts by weight) |  | 206 | 380 | 272 | 190 | 370 | 450 | 400 |
|  | Particle size distribution of filler (μm) |  | 0.7-27 | 0.7-27 | 0.7-27 | 0.2-3 | 1-40 | 0.7-27 | 1.0-60 |
|  | Average particle diameter of filler (μm) |  | 4.5 | 4.5 | 4.5 | 0.4 | 15.0 | 4.5 | 8.0 |
|  | Fine particle filler (parts by weight) |  | 16 | 47 | 28 | 28 | 28 | 0 | 28 |
|  | Averge particle diameter of fine particle filler (μm) |  | 0.040 | 0.040 | 0.040 | 0.040 | 0.040 | — | 0.040 |
|  | Oxidant | BPO (parts by weight) | 1.5 | 1.5 | 1.5 | 1.5 | 1.5 | 1.5 | 1.5 |
|  | Photopolymerization catalyst | CQ/OBA (parts by weight) | 1.5/1.5 | 1.5/1.5 | 0/0 | 1.5/1.5 | 1.5/1.5 | 1.5/1.5 | 1.5/1.5 |
|  | Viscosity (P): 25° C. |  | 320 | 520 | 420 | 540 | 400 | 330 | 400 |
| Second paste | (Meth)acrylate monomer | Bis-MEPP (parts by weight) | 90 | 90 | 90 | 90 | 90 | 90 | 90 |
|  |  | 3G (parts by weight) | 10 | 10 | 10 | 10 | 10 | 10 | 10 |
|  | Filler (parts by weight) |  | 180 | 338 | 248 | 190 | 370 | 450 | 400 |
|  | Particle size distribution of filler (μm) |  | 0.6-21 | 0.6-21 | 0.6-21 | 0.2-3 | 1-40 | 0.6-21 | 1.0-60 |
|  | Average particle diameter of filler (μm) |  | 2.5 | 2.5 | 2.5 | 0.4 | 15.0 | 2.5 | 8.0 |
|  | Fine particle filler (parts by weight) |  | 12 | 38 | 22 | 22 | 22 | 0 | 22 |
|  | Averge particle diameter of fine particle filler (μm) |  | 0.040 | 0.040 | 0.040 | 0.040 | 0.040 | — | 0.040 |
|  | Reductant | DEPT (parts by weight) | 1.7 | 1.7 | 1.7 | 1.7 | 1.7 | 1.7 | 1.7 |
|  | Photopolymerization catalyst | CQ/DMA (parts by weight) | 0.6/2.0 | 0.6/2.0 | 0/0 | 0.6/2.0 | 0.6/2.0 | 0.6/2.0 | 0.6/2.0 |
|  | Viscosity (P): 25° C. |  | 230 | 430 | 330 | 520 | 340 | 300 | 330 |

TABLE 4

| Evaluation results | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|
| Viscosity of mixture (P): 25° C. | 270 | 480 | 380 | 530 | 370 | 320 | 350 |
| Extruding force (N) | 42 | 289 | 110 | 330 | 120 | 140 | 200 |
| Extruding property | a | c | a | c | a | a | a |
| Filling property for root canal | a | b | a | b | a | a | a |
| Flow score (mm) | 3.0 | 0 | 0 | 0 | 3.5 | 4.5 | 4.2 |
| Mottling of mixture before curing | a | b | b | a | a | a | a |
| Sensitivity to ambient light (sec.) | 40 | 40 | — | 45 | 45 | 45 | 45 |

TABLE 4-continued

| Evaluation results | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|
| Flexural strength (MPa) | 118 | 133 | Not cured | 95 | 132 | 117 | 111 |
| Flexural modulus (GPa) | 8 | 12 | Not cured | 6 | 11 | 7 | 6 |

As shown in Tables 1 and 2, in the divided type dental polymeric core build-up material of this invention (according to any of Embodiments 1 through 9), the extruding property of the pastes and the filling property for a root canal forming portion are good, the pastes minimally sag, and the flexural strength and the flexural modulus of the polymerically cured substance are high. It is understood from these results that the divided type dental polymeric core build-up material of this invention has high operability of the pastes and forms the polymeric cured substance with a good mechanical property. It is understood from the results of the test for the mottling of the mixture obtained before curing and the test for the sensitivity to the ambient light of the divided type dental polymeric core build-up material of Embodiment 1 and the divided type dental polymeric core build-up material of Embodiment 4 or 5 that the photopolymerization catalyst is preferably included dividedly in the respective pastes.

On the other hand, as shown in Tables 3 and 4, in the divided type dental polymeric core build-up material of Comparative Example 1 (corresponding to an example where one of the pastes has a too low viscosity), although the extruding property and the filling property for a root canal forming portion are good, it easily sags and has a poor mechanical property. In the divided type dental polymeric core build-up material of Comparative Example 2 (corresponding to an example where one of the pastes has a too high viscosity), although it minimally sags and has a good mechanical property, the extruding property and the filling property for a root canal forming portion are not good. In the divided type dental polymeric core build-up material of Comparative Example 3 (corresponding to an example where none of the pastes includes a photopolymerization catalyst), although the extruding property and the filling property for a root canal forming portion are good and it minimally sags, it cannot be suitably used as a core build-up material because it cannot be photopolymerically cured (namely, cannot form a photopolymerically cured substance with a good mechanical property). In the divided type dental polymeric core build-up material of Comparative Example 4 (corresponding to an example where the average particle diameter of the filler is too small and the viscosities of the pastes are too high), although it minimally sags, the extruding property and the filling property are not good and the polymerically cured substance does not exhibit a good mechanical property. In the divided type polymeric core build-up material of Comparative Example 5 (corresponding to an example where the average particle diameter of the filler is too large), although the extruding property, the filling property and the mechanical property of the polymerically cured substance are good, it easily sags and hence cannot be suitably used as a core build-up material. In the divided type dental polymeric core build-up material of Comparative Example 6 (corresponding to an example where no fine particle filler is included), although the extruding property and the filling property are good, it easily sags and the polymerically cured substance does not exhibit a good mechanical property. In the divided type dental polymeric core build-up material of Comparative Example 7 (corresponding to an example where the particle size distribution of the filler covers a region of a large particle diameter), although the extruding property and the filling property are good, it easily sags and the polymerically cured substance does not exhibit a good mechanical property.

Reference Example 1

A mixing device including a pair of cylindrical polyolefin containers (each with an internal volume of 1.5 ml, an inner diameter of 6.5 mm and an out diameter of 7.5 mm) arranged in parallel, a mixer provided at the front ends of the containers and an extruder composed of a pair of cylindrical extruding members respectively fit in the containers from the rear ends thereof and fixedly connected to each other was prepared. The mixer included a mixing part (manufactured by MIXPAC SYSTEMS AG, trade code "ML-2.5-08-D") having 8 agitating blades (elements) and a plastic discharging part (manufactured by MIXPAC SYSTEMS AG, trade code "IOT212-20") provided at the tip of the mixing part and bent at an angle of 60 degrees, and the wall of the mixer was made of a member with an ambient light transmitting property. This mixing device had a size and a volume suitable to a form to be thrown out after use for one core build-up, namely, suitable to use as the so-called disposable type. Since the mixing device can come into contact with lips or a mouth cavity wall during the core build-up, the mixing device of the disposable type is preferably used for preventing infection.

After charging 1.2 ml each of the first paste and the second paste of Embodiment 1 dividedly in the containers of the mixing device, the pair of extruding members were made to enter the pair of containers, so as to extrude the pastes contained in the containers into the mixing part, and the two pastes were mixed in the mixing part so that the thus obtained mixture could be discharged from the discharging part.

The test for the extruding force, the test for the filling property, the test for the slump property, the test for the mottling, the test for the sensitivity to the ambient light and the evaluation test for the mechanical property of a polymerically cured substance all described above were performed in the same manner as described above on the core build-up material of Embodiment 1 except that the aforementioned disposable type mixing device was used instead of a commercially available mixing device. The evaluation results were as follows:

Extruding force: 40 N (the extruding property "a"); the filling property: "a"; the flow score: 0 mm; the mottling: "a"; the sensitivity to the ambient light: 40 sec.; the flexural strength: 155 MPa; and the flexural modulus: 12 GPa.

The invention claimed is:
1. A divided dental polymeric core build-up material comprising a first paste (A) and a second paste (B),
wherein each of said first paste (A) and said second paste (B) is a paste that includes a (meth)acrylate monomer (I), and a filler composition consisting essentially of a first and second filler, wherein the first filler (II) has a particle size distribution within a range of 0.1 through 40

μm and an average particle diameter of 0.7 through 10 μm and is present in an amount of 190 to 370 parts by weight based on 100 parts by weight of the (meth)acrylate monomer (I), and the second-filler (III) has an average particle diameter of primary particles of 0.005 through 0.045 μm in an amount of 3 to 60 parts by weight based on 100 parts by weight of the (meth)acrylate monomer (I), and has a viscosity at 25° C. of 280 through 470 P, one of said first paste (A) and said second paste (B) includes an oxidant (IV) and the other includes a reductant (V), and at least one of said first paste (A) and said second paste (B) includes a photopolymerization catalyst (VI).

2. A divided dental polymeric core build-up material comprising a first paste (B) and a second paste (B), wherein each of said first paste (A) and said second paste (B) is a paste that is obtained by mixing at least a (meth)acrylate monomer (I), and a filler composition consisting essentially of a first and second filler, wherein the first filler (II) has a particle size distribution within a range of 0.1 through 40 μm and an average particle diameter of 0.7 through 10 μm in an amount of 190 to 370 parts by weight based on 100 parts by weight of the (meth)acrylate monomer (I), and the second filler (III) has an average particle diameter of primary particles of 0.005 through 0.045 μm in an amount of 3 to 60 parts by weight based on 100 parts by weight of the (meth)acrylate monomer (I), and has a viscosity at 25° C. of 280 through 470 P, one of said first paste (A) and said second paste (B) includes an oxidant (IV) and the other includes a reductant (V), and at least one of said first paste (A) and said second paste (B) includes a photopolymerization catalyst (VI).

3. The divided dental polymeric core build-up material according to claim 2, wherein said filler (II) has a particle size distribution within a range of 0.5 through 30 μm and an average particle diameter of 0.7 through 10 μm.

4. The divided dental polymeric core build-up material according to claim 2, wherein said filler (II) has a particle size distribution within a range of 0.5 through 30 μm and an average particle diameter of 1.5 through 10 μm.

5. The divided type dental polymeric core build-up material according to claim 2, wherein a mixture of said first paste (A) and said second paste (B) has a viscosity at 25° C. of 280 through 470 P.

6. The divided dental polymeric core build-up material according to claim 2, wherein both of said first paste (A) and said second paste (B) include said photopolymerization catalyst (VI).

7. The divided dental polymeric core build-up material according to claim 6, wherein ratios of said oxidant (IV) and said photopolymerization catalyst (VI) included in said first paste (A) are 0.01 through 5 parts by weight and 0.01 through 5 parts by weight based on 100 parts by weight of the (meth)acrylate monomer (I) included in said first paste (A), and ratios of said reductant (V) and said photopolymerization catalyst (VI) included in said second paste (B) are 0.01 through 5 parts by weight and 0.01 through 5 parts by weight based on 100 parts by weight of the (meth)acrylate monomer (I) included in said second paste (B).

8. The divided dental polymeric core build-up material according to claim 7, wherein a weight ratio between said first paste (A) and said second paste (B) is 1:2 through 2:1.

9. The divided dental polymeric core build-up material according to claim 3, wherein a mixture of said first paste (A) and said second paste (B) has a viscosity at 25° C. of 280 through 470 P.

10. The divided dental polymeric core build-up material according to claim 4, wherein a mixture of said first paste (A) and said second paste (B) has a viscosity at 25° C. of 280 through 470 P.

11. The divided dental polymeric core build-up material according to claim 3, wherein both of said first paste (A) and said second paste (B) include said photopolymerization catalyst (VI).

12. The divided dental polymeric core build-up material according to claim 4, wherein both of said first paste (A) and said second paste (B) include said photopolymerization catalyst (VI).

13. The divided dental polymeric core build-up material according to claim 5, wherein both of said first paste (A) and said second paste (B) include said photopolymerization catalyst (VI).

14. The divided dental polymeric core build-up material according to claim 9, wherein both of said first paste (A) and said second paste (B) include said photopolymerization catalyst (VI).

15. The divided dental polymeric core build-up material according to claim 10, wherein both of said first paste (A) and said second paste (B) include said photopolymerization catalyst (VI).

* * * * *